United States Patent [19]

Christidis et al.

[11] 4,454,155
[45] Jun. 12, 1984

[54] PHARMACEUTICAL COMPOSITIONS CONTAINING A MONO-SUBSTITUTED DERIVATIVE OF 4-PHENYL-4-OXOBUTEN-2-OIC ACID, AND METHODS OF USING THEM IN TREATING GASTRIC AND GASTRODUODENAL AILMENTS

[75] Inventors: Yani Christidis, Paris, France; Fernando Barzaghi, Milan, Italy

[73] Assignee: Roussel UCLAF, Paris, France

[21] Appl. No.: 435,623

[22] Filed: Oct. 20, 1982

[30] Foreign Application Priority Data

Oct. 22, 1981 [FR] France ................. 81 19832

[51] Int. Cl.$^3$ .......................................... A61K 31/19
[52] U.S. Cl. ..................................... 424/317; 424/308
[58] Field of Search ............................. 424/317, 308

[56] References Cited

U.S. PATENT DOCUMENTS

| | | | |
|---|---|---|---|
| 2,532,579 | 12/1950 | Thomas | 167/30 |
| 2,562,208 | 7/1951 | Papa et al. | 167/22 |
| 3,753,997 | 8/1973 | Ash et al. | . |
| 3,763,148 | 10/1973 | Ash et al. | . |
| 3,846,470 | 11/1974 | Raube et al. | 260/465 E |
| 3,910,959 | 10/1975 | Vallet | 260/340.5 |
| 3,940,404 | 2/1976 | Ash et al. | . |
| 3,940,487 | 2/1976 | La Croix et al. | 424/282 |
| 3,943,169 | 3/1976 | Murata et al. | 424/317 |
| 3,953,463 | 4/1976 | Ash et al. | . |
| 4,008,323 | 2/1977 | Crousse et al. | 424/317 |
| 4,017,517 | 4/1977 | Murata et al. | 260/340.5 |
| 4,058,558 | 11/1977 | Crousse et al. | 424/317 |

FOREIGN PATENT DOCUMENTS

| | | | |
|---|---|---|---|
| 1282644 | 9/1962 | Fed. Rep. of Germany | . |
| 2047806 | 4/1972 | Fed. Rep. of Germany | . |
| 2103749 | 8/1972 | Fed. Rep. of Germany | . |
| 2501834 | 7/1975 | Fed. Rep. of Germany | . |
| 1566212 | 5/1969 | France | . |
| 1566213 | 5/1969 | France | . |
| 2132354 | 12/1972 | France | . |
| 2270856 | 12/1975 | France | . |
| 55-36434 | 3/1980 | Japan | . |
| 591415 | 9/1977 | Switzerland | . |
| 588108 | 6/1947 | United Kingdom | 424/317 |
| 1387733 | 3/1975 | United Kingdom | 424/317 |

OTHER PUBLICATIONS

*Journal of American Pharmaceuticl Association*, vol. 37, No. 11, Nov. 1948, pp. 439–449.
*Chemical Abstracts*, vol. 88, No. 5, Jan. 30, 1978, Abstract 37442p.
*Journal of the American Chemical Society*, vol. 71, No. 4, Apr., 1949, F. K. Kirchner et al, pp. 1210–1213.
*Journal of the American Chemical Society*, vol. 70, No. 10, Oct. 1948, D. Papa et al, pp. 3356–3360.
*European Journal of Medical Chemistry Chimica Therapeutica*, vol. 12, Jan.–Feb. 1977, pp. 17–20.
*European Journal of Medical Chemistry Chimica Therapeutica*, vol. 13, No. 3, May–Jun. 1978, H. Orzalesi et al, pp. 259–264.
*Beilstein*, vol. 19, p. 312.
*Journal of Pharmaceutical Sciences*, vol. 66, No. 4, Apr. 1977, pp. 466–476, Child, Ralph G. et al., "Fenbufen, a New Anti-Inflammatory Analgesic: Synthesis and Structure–Activity Relationships of Analogs".
*Journal of Medicinal Chemistry*, vol. 15, No. 9, Sep. 1972, pp. 918–922, Markovac, A., et al., "Antimalarials 3, 2,6--Bis(aryl)-4-pyridinemethanols with Trifluoromethyl Substituents".
*Journal of Organic Chemistry*, vol. 35, No. 5, May 1970, pp. 1367–1376, Pettit, George R., et al., "Bufadienolides 1., Introduction and Base–Catalyzed Condensation of Methyl Ketonds with Glyoxylic Acid".
*J.A.C.S.*, vol. 46, No. 10, Oct. 1924, pp. 2319–2326, Rice, Grace Potter, "The Isomeric Esters of Para–Ethoxy–Benzoylacrylic Acid".

*Primary Examiner*—Frederick E. Waddell
*Attorney, Agent, or Firm*—Stevens, Davis, Miller & Mosher

[57] ABSTRACT

Pharmaceutical compositions containing a compound of the formula (I):

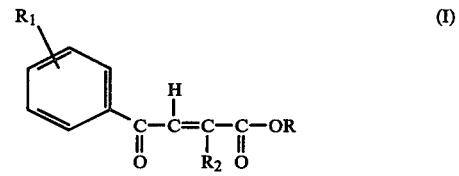

in which R represents a hydrogen atom or an alkyl radical containing from 1 to 8 carbon atoms, $R_1$ represents a hydroxy radical in 2-position or an alkoxy radical in 4-position containing from 1 to 8 carbon atoms, and $R_2$ represents a hydrogen atom or an alkyl radical containing from 1 to 8 carbon atoms. Pharmaceutically acceptable alkali metal, alkaline earth metal, ammonium or amine salts of the compounds of formula (I) in which R represents a hydrogen atom may also be included in the compositions. Such compositions are useful in treating hyperchlorhydria, gastric or gastroduodenal ulcers, gastritis, hiatal hernias, and gastric or gastroduodenal ailments accompanied by gastric hyperacidity.

15 Claims, No Drawings

PHARMACEUTICAL COMPOSITIONS CONTAINING A MONO-SUBSTITUTED DERIVATIVE OF 4-PHENYL-4-OXOBUTEN-2-OIC ACID, AND METHODS OF USING THEM IN TREATING GASTRIC AND GASTRODUODENAL AILMENTS

The present invention relates to pharmaceutical compositions including certain derivatives of 4-phenyl-4-oxobuten-2-oic acid as medicaments in pharmaceutical compositions.

An object of the invention is to provide pharmaceutical compositions which include a compound of formula (I):

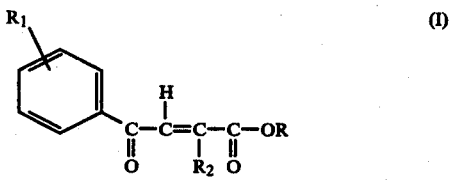

in which R represents a hydrogen atom or an alkyl radical containing from 1 to 8 carbon atoms, $R_1$ represents a hydroxy radical in the 2-position or an alkoxy radical in the 4-position containing from 1 to 8 carbon atoms, and $R_2$ represents a hydrogen atom or an alkyl radical containing from 1 to 8 carbon atoms, as well as the pharmaceutically acceptable alkali metal, alkaline earth metal, ammonium or amine salts of the compound of formula (I) in which R represents a hydrogen atom.

When $R_1$ represents an alkoxy radical, the radical is preferably the methoxy, ethoxy or propoxy radical.

When $R_2$ represents an alkyl radical, it is preferably the methyl radical.

When R represents an alkyl radical, it is preferably the methyl, ethyl, n-propyl, isopropyl, n-butyl, isobutyl, terbutyl or pentyl radical.

The alkali metal or alkaline earth metal salts of the compounds of formula (I) in which R represents a hydrogen atom may be the sodium, potassium, lithium or calcium salts.

The amine salts of the compounds of formula (I) in which R represents a hydrogen atom are the usual amine salts. These amines are monoalkyl-amines such as methyl amine, ethyl amine an propyl amine, dialkyl-amines such as, for instance, dimethylamine, diethylamine and di-n-propylamine, and trialkylamines such as triethylamine. Piperidine, morpholine, piperazine and pyrrolidine are further examples.

More particularly, the invention has as its object pharmaceutical compositions containing a compound of formula (I) in which R represents a hydrogen atom as well as the pharmaceutically acceptable alkali metal, alkaline earth metal, ammonium or amine salts as well as those in which $R_2$ represents a hydrogen atom.

Among the preferred embodiments of the invention, particular mention may be made of the compounds in which $R_1$ represents a hydroxy radical in the 2-position as well as those in which $R_1$ represents a methoxy radical in the 4-position.

Particularly preferred are the compounds mentioned below in the examples and in particular 4-(2-hydroxyphenyl)-4-oxobuten-2-oic acid as well as its pharmaceutically acceptable alkali metal, alkaline earth metal, ammonium or amine salts.

The compounds of formula I have useful pharmacological properties. In particular, they display substantial anti-ulcer activity in treating ailments of the digestive tract. Furthermore, when contacted with the gastric mucosa, they exhibit gastric anti-secretion activity as well as cytoprotective activity. The compounds of the invention can therefore be used in therapy, and in particular, for treating hyperchlorhydria, gastric and gastroduodenal ulcers, gastritis, hiatal hernias, and gastric and gastroduodenal ailments accompanied by gastric hyperacidity. Of course, compositions including these compounds are also useful in these treatments.

The dose, which varies in accordance with the compound used and the ailment in question, may range, for instance, between 0.05 g and 2 g per day for adults, per os.

As discussed previously, the object of the present invention is pharmaceutical compositions which contain one of the above compounds as an active principle. The compositions are produced in such a manner that they can be administered by either a digestive (oral or rectal) or parenteral route.

The compositions may be solid or liquid and can be present in the pharmaceutical forms commonly used in human medicine such as, for example, simple or coated tablets, capsules, granules, suppositories and injectable preparations. These may be prepared by the customary methods.

The active principle or principles may be incorporated in excipients generally employed in these types of pharmaceutical compositions such as talc, gum arabic, lactose, starch, magnesium stearate, cocoa butter, aqueous or nonaqueous vehicles, fats of animal or vegetable origin, paraffin derivatives, glycols, various wetting, dispersing or emulsifying agents and preservatives.

The compounds of formula I are generally known compounds which can be prepared by the methods described by Ziegler et al, Liebigs Annalen 9, 1552, (1973) or by Papa et al, J. Am. Chem. Soc. 70, 3356 (1948).

The compounds of formula (I) in which R and $R_2$ each represent a hydrogen atom may be prepared, for instance, by condensation of glyoxylic acid with an acetophenone substituted on the phenyl ring, in the presence of acetic anhydride or another dehydrating agent.

The esters of formula (I) as well as the salts of compounds of formula (I) (when R represents a hydrogen atom) can be prepared using the standard techniques known to those of ordinary skill in the art.

The following examples illustrate the invention, without, however, limiting it.

EXAMPLE 1

4-(2-hydroxyphenyl)-4-oxobuten-2-oic acid

The compound was prepared by the process described in Liebigs Annalen 9, 1552, (1973). MP=172°–175° C.

EXAMPLE 2

4-(4-methyoxyphenyl)-4-oxobuten-2-oic acid

The compound was prepared by the process described by Papa et al, J. Am. Chem. Soc. 70, 3356 (1948).

PHARMACEUTICAL FORMS

EXAMPLE 3

Tablets

Tablets were prepared having the formula:
Compound of Example 1: 100 mg,
Excipient q.s. for a finished tablet of: 300 mg.
(Details of excipient: lactose, wheat starch, processed starch, rice starch, magnesium stearate, talc).

EXAMPLE 4

Capsules

Capsules were prepared having the following formula:
Compound of Example 1: 100 mg,
Excipient q.s. for a finished capsule of: 300 mg.
(Details of excipient: talc, magnesium stearate, aerosil).

PHARMACOLOGICAL STUDY (1) Determination of the gastric anti-secretory activity The technique used is described by H. Shay et al in Gastroenterology 5, 43 (1945).

Male rats were used, each having a weight of about 200 g (ten animals per lot), which had been without food for 48 hours but were allowed 8% glucose solution ad libitum. After the rats were slightly anesthetized with ether, the pylorus of each was ligated. At the end of the operation, different doses of the product to be tested, or in the case of the control animals a 0.5% carboxymethyl cellulose solution, were administered intraduodenally, whereupon the abdominal incision was sutured.

Three hours later, the animals were sacrificed and their stomachs removed after ligating the esophagus. The gastric juice was removed and centrifuged. The volume of gastric juice obtained was then measured and the total acidity of the gastric juice obtained was established by titrating a 100 μL sample of gastric juice to a pH of 7 with 1/10 N Sodium hydroxide aqueous solution. The total acidity was determined.

The percentage of variation of total acidity between the results from test animals and results from control animals were calculated. The results are set forth in the table of results below.

(2) Determination of the anti-ulcer activity

Stress Ulcer

The technique consists in inducing ulcers in the stomachs of rats by stress (stress and cold). The technique used is described by E. C. Senay and R. J. Levine, Proc. Soc. Ex. Biol. 124, 1221 (1967).

Female rats of 150 g (5 animals per lot) were used which had fasted for 48 hours with water ad libitum and glucose solution for 8 hours. The animals were given the test product, or a 0.5% solution of carboxymethyl cellulose in the case of the control animals, by esophageal tube. Two hours later, the animals were wrapped in a jacket of netting. Their paws were bound and the entire unit was placed in a refrigerator at 8° C. for two hours. The rats were freed and killed with ether. Their stomachs were removed, opened along the greater curvature and examined with a binocular magnifier. The seriousness of the lesions was rated from 0 to 3 for each stomach.

The average intensity of the ulcerations was calculated for each lot of rats. The difference in the degree of ulceration between test animals and control animals was determined and calculated as a percentage. The results are set forth in the following table of results.

(3) Determination of the acute toxicity

The $LD_{50}$ was evaluated after administration of the product per os in mice.

| | | Results Anti-secretory and anti-ulcer activity (% variation as compared with the controls) | | |
|---|---|---|---|---|
| Compound of Example | $LD_{50}$ mg/kg per os | Dose mg/kg | Acid Concentration | Ulceration |
| 1 | 350 | 10 | −65 | −35 |
| 2 | 500 | 10 | −66 | −73 |

What is claimed is:

1. A method for treating a patient suffering from hyperchlorhydria, gastric or gastroduodenal ulcers, gastritis hiatal hernias, or gastric ailments accompanied by gastric hyperacidity comprising:
administering to said patient a therapeutically effective amount of a compound of formula (I):

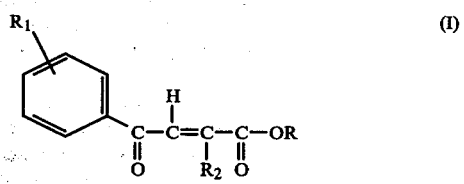

in which R represents a hydrogen atom or an alkyl radical containing from 1 to 8 carbon atoms, $R_1$ represents a hydroxy radical in the 2-position or an alkoxy radical in the 4-position containing from 1 to 8 carbon atoms, and $R_2$ represents a hydrogen atom or an alkyl radical containing from 1 to 8 carbon atoms or of a pharmaceutically acceptable alkali metal, alkaline earth metal ammonium or amine salt of a compound of formula (I) wherein R represents a hydrogen atom.

2. A method as claimed in claim 1 comprising administering a therapeutically effective amount of a compound of formula (I) wherein R represents a hydrogen atom, or of a pharmaceutically acceptable alkali metal, alkaline earth metal, ammonium or amine salt of the compound of formula (I) wherein R represents a hydrogen atom.

3. A method as claimed in claim 1, wherein $R_2$ represents a hydrogen atom.

4. A method as claimed in claim 2, wherein $R_2$ represents a hydrogen atom.

5. A method as claimed in claim 1, wherein $R_1$ represents a hydroxy radical in the 2-position.

6. A method as claimed in claim 2, wherein $R_1$ represents a hydroxy radical in the 2-position.

7. A method as claimed in claim 3, wherein $R_1$ represents a hydroxy radical in the 2-position.

8. A method as claimed in claim 4, wherein $R_1$ represents a hydroxy radical in the 2-position.

9. A method as claimed in claim 1, wherein $R_1$ represents a methoxy radical in the 4-position.

10. A method as claimed in claim 2, wherein $R_1$ represents a methoxy radical in the 4-position.

11. A method as claimed in claim 3, wherein $R_1$ represents a methoxy radical in the 4-position.

12. A method as claimed in claim 4, wherein $R_1$ represents a methoxy radical in the 4-position.

13. A method as claimed in claim 1, wherein the compound of formula (I) is 4-(2-hydroxyphenyl)-4-oxobuten-2-oic acid or a pharmaceutically acceptable alkali metal, alkaline earth metal, ammonium or amine salt thereof.

14. A method as claimed in claim 1, wherein said compound is administered orally or rectally.

15. A method as claimed in claim 1, wherein said compound is administered parenterally.